United States Patent
Koch et al.

(10) Patent No.: US 7,144,891 B2
(45) Date of Patent: Dec. 5, 2006

(54) BENZO[B]PYRANO[3,2- H ]ACRIDIN-7-ONE CINNAMATE COMPOUNDS

(75) Inventors: Michel Koch, La Celle Saint Cloud (FR); François Tillequin, Paris (FR); Sylvie Michel, Paris (FR); John Hickman, Paris (FR); Alain Pierre, Les Alluets le Roi (FR); Stéphane Léonce, Versailles (FR); Bruno Pfeiffer, Saint Leu la Foret (FR); Laurence Kraus-Berthier, Colombes (FR)

(73) Assignees: Les Laboratoires Servier, Courbevoie (FR); Centre National de la Recherche Scientifique, Paris (FR); University Rene Descartes Paris V, Paris (FR)

( * ) Notice: Subject to any disclaimer, the term of this patent is extended or adjusted under 35 U.S.C. 154(b) by 0 days.

(21) Appl. No.: 11/313,386

(22) Filed: Dec. 21, 2005

(65) Prior Publication Data
US 2006/0135545 A1    Jun. 22, 2006

(30) Foreign Application Priority Data
Dec. 22, 2004   (FR) ................... 04 13682

(51) Int. Cl.
*A61K 31/4741*   (2006.01)
*C07D 491/02*    (2006.01)
(52) U.S. Cl. ........................................ 514/280; 546/47
(58) Field of Classification Search ................ 514/280; 546/47
See application file for complete search history.

(56) References Cited
U.S. PATENT DOCUMENTS
6,503,919 B1 * 1/2003 Koch et al. .................. 514/279

* cited by examiner

Primary Examiner—Charanjit S. Aulakh
(74) Attorney, Agent, or Firm—Hueschen and Sage

(57) ABSTRACT

A compound selected from those of formula (I):

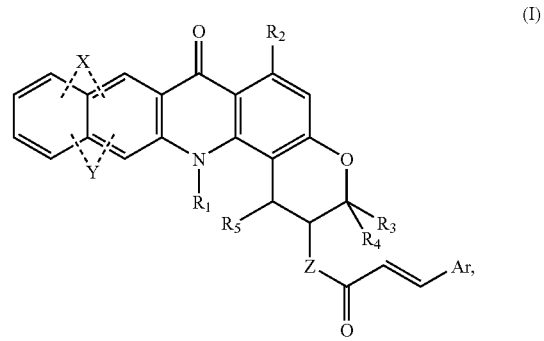

wherein:
X and Y represent a group selected from hydrogen, halogen, alkoxy, nitro, cyano, alkyl, alkenyl, polyhaloalkyl and —$NR_aR_b$ wherein $R_a$ and $R_b$ are as defined in the description, Z represents oxygen or $NR_c$ wherein $R_c$ is as defined in the description, Ar represents aryl or heteroaryl, $R_1$ represents hydrogen or alkyl, $R_2$ represents a group selected from hydrogen, alkyl, —$OR_a$ and —$NR_aR_b$ wherein $R_a$ and $R_b$ are as defined in the description, $R_3$ and $R_4$ represent hydrogen or alkyl, $R_5$ represents hydrogen, $OR_c$, $NR_cR_d$, $W_1$—C($W_2$)—U—V, $W_1$—C($W_2$)—$W_3$-$T_1$ or Z-CO—CH=CHAr wherein $R_c$, $R_d$, $W_1$, $W_2$, $W_3$, U, V, T, Z and Ar are as defined in the description, its isomers, and addition salts thereof with a pharmaceutically acceptable acid or base, and medicinal products containing the same which are useful in the treatment of cancer.

12 Claims, No Drawings

BENZO[B]PYRANO[3,2- H ]ACRIDIN-7-ONE CINNAMATE COMPOUNDS

FIELD OF THE INVENTION

The compounds of the invention are derivatives of acronycine, an alkaloid which has anti-tumour properties that have been demonstrated in experimental models (*J. Pharm. Sci.*, 1966, 55 (8), 758–768). However, despite having quite a broad spectrum of activity, acronycine is of low potency and moderate activity. The solubility of the compound is, moreover, low, which limits its bioavailability, as well as its use in pharmaceutical compositions for administration by the intravenous route.

Various modifications have been made to the molecule, for example those described in *J. Med. Chem.*, 1996, 39, 4762–4766, EP 1 042 326, EP 1 061 081 or EP 1 297 835, allowing a significant improvement in the potency, anti-tumour efficacy and solubility of the products. Nevertheless, anti-cancer therapeutic requirements call for the constant development of new anti-tumour agents with the aim of obtaining medicaments that are simultaneously more active and better tolerated. More specifically, solid tumours constitute a major problem for anti-cancer chemotherapy because of their intrinsic and/or acquired resistance to existing compounds. It is therefore of prime importance to have access to the widest possible range of compounds exhibiting powerful cytotoxic activity in order to have available the most effective treatments for the totality of tumour disorders.

Besides the fact that the compounds of the invention are new, they have surprising in vitro and in vivo cytotoxic activity which is greater than that observed hitherto. The compounds discovered by the Applicant accordingly have anti-tumour properties that make them especially useful in the treatment of cancers. Among the types of cancer which may be treated by the compounds of the present invention there may be mentioned, without implying any limitation, adenocarcinonmas and carcinomas, sarcomas, gliomas and leukaemias.

DETAILED DESCRIPTION OF THE INVENTION

More specifically, the present invention relates to compounds of formula (I):

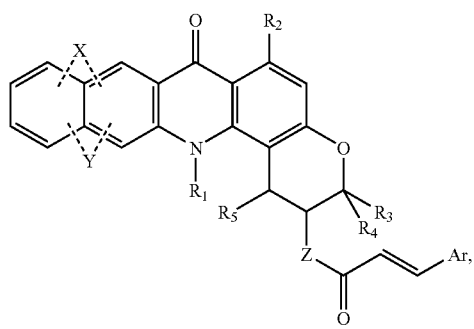

wherein:
X and Y, which may be the same or different, represent, each independently of the other, a group selected from:
hydrogen and halogen atoms,
hydroxy, linear or branched ($C_1$–$C_6$)alkoxy, nitro, cyano, linear or branched ($C_1$–$C_6$)alkyl (optionally substituted by one or more groups selected from hydroxy and halogen) and linear or branched ($C_2$–$C_6$)alkenyl groups and
a group of formula —$NR_aR_b$ wherein:
$R_a$ and $R_b$, which may be the same or different, represent, each independently of the other, a group selected from a hydrogen atom and a linear or branched ($C_1$–$C_6$)alkyl group,
or $R_a$ and $R_b$, together with the nitrogen atom carrying them, form a monocyclic, 5- to 7-membered heterocycle optionally containing within the cyclic system a second hetero atom selected from oxygen and nitrogen,
it being understood that the substituents X and Y may be present, each independently of the other, on either of the two adjacent benzene rings,
Z represents an oxygen atom or $NR_c$ wherein $R_c$ represents a group selected from a hydrogen atom, a linear or branched ($C_1$–$C_6$)alkyl group, an aryl group and an aryl-($C_1$–$C_6$)alkyl group in which the alkyl moiety is linear or branched,
Ar represents an aryl or heteroaryl group,
$R_1$ represents a hydrogen atom or a linear or branched ($C_1$–$C_6$)alkyl group,
$R_2$ represents a group selected from a hydrogen atom, a linear or branched ($C_1$–$C_6$)-alkyl group, —$OR_a$ and —$NR_aR_b$ wherein $R_a$ and $R_b$ are as defined hereinbefore,
$R_3$ and $R_4$, which may be the same or different, represent, each independently of the other, a hydrogen atom or a linear or branched ($C_1$–$C_6$)alkyl group,
$R_5$ represents a group selected from:
1) a hydrogen atom,
2) $OR_c$ and $NR_cR_d$ groups wherein:
$R_c$ is as defined hereinbefore and $R_d$ is as defined for $R_c$,
3) $W_1$—C($W_2$)—U—V wherein:
α) $W_1$ represents an oxygen atom or $NR_c$ (wherein $R_c$ is as defined hereinbefore),
β) $W_2$ represents an oxygen atom,
γ) U represents a single bond or a linear or branched ($C_1$–$C_8$)alkylene chain or a linear or branched ($C_2$–C8)alkenylene chain,
δ) V represents a group selected from:
a hydrogen atom,
aryl and heteroaryl groups,
$OR_c$, $CO_2R_c$, $COR_c$, $CONR'_aR'_b$, $NR'_aR'_b$, $N(R_c)$—$CO_2R'_c$ and $N(R_c)$—$COR'_c$ groups wherein $R_c$ is as defined hereinbefore, $R'_c$ is as defined for $R_c$, and $R'_a$ and $R'_b$, which may be the same or different, represent, each independently of the other, a group selected from a hydrogen atom, a linear or branched ($C_1$–$C_6$) alkyl group, an aryl group and an aryl-($C_1$–$C_6$) alkyl group in which the alkyl moiety is linear or branched or $R'_a$ and $R'_b$, together with the nitrogen atom carrying them, form a monocyclic, 5- to 7-membered heterocycle optionally containing within the cyclic system a second hetero atom selected from oxygen and nitrogen,
4) $W_1$—C($W_2$)—$W_3$-$T_1$ wherein:
α) $W_1$ and $W_2$ are as defined hereinbefore,
β) $W_3$ represents an oxygen atom or $NR_c$ wherein $R_c$ is as defined hereinbefore, γ) $T_1$ represents a group selected from:
  a hydrogen atom,
  linear or branched ($C_1$–$C_6$)alkyl,
  linear or branched ($C_2$–$C_6$)alkenyl,
  aryl, aryl-($C_1$–$C_6$)alkyl in which the alkyl moiety is linear or branched,
  a linear or branched ($C_1$–$C_6$)alkylene chain and a linear or branched ($C_2$–$C_6$)alkenylene chain, each of which is substituted by a group $OR_c$ wherein $R_c$ is as defined hereinbefore or by $NR'_aR'_b$ wherein $R'_a$ and $R'_b$ are as defined hereinbefore, 5) Z-CO—CH=CHAr wherein Z and Ar are as defined hereinbefore, to their enantiomers and diastereoisomers, when they exist, and also addition salts thereof with a pharmaceutically acceptable acid or base, and also hydrates thereof and solvates thereof, it being understood that:

aryl means a phenyl or naphthyl group optionally containing one or more, identical or different, substituents selected from linear or branched ($C_1$–$C_6$)alkyl (optionally substituted by one or more hydroxy or halogen groups), hydroxy, halogen, carboxy, nitro, amino, linear or branched mono($C_1$–$C_6$)alkylamino, di($C_1$–$C_6$)alkylamino wherein each alkyl moiety may be linear or branched, linear or branched ($C_1$–$C_6$)alkoxy, linear or branched ($C_1$–$C_6$)acyl and linear or branched ($C_1$–$C_6$)alkyl-carbonyloxy, heteroaryl means a 5- to 12-membered group which either is monocyclic and aromatic or is bicyclic with at least one of the rings being of aromatic character, and which contains one, two or three hetero atoms selected from oxygen, nitrogen and sulphur, it being understood that the heteroaryl group may be optionally substituted by one or more identical or different atoms or groups selected from halogen atoms and linear or branched ($C_1$–$C_6$)alkyl groups (optionally substituted by one or more hydroxy or halogen groups), hydroxy groups, linear or branched ($C_1$–$C_6$)alkoxy groups, and amino groups (optionally substituted by one or two linear or branched ($C_1$–$C_6$)alkyl groups).

Among the heteroaryl groups there may be mentioned, without implying any limitation, thienyl, pyridyl, furyl, pyrrolyl, imidazolyl, oxazolyl, isoxazolyl, thiazolyl, isothiazolyl, quinolyl, isoquinolyl and pyrimidinyl groups.

Among the monocyclic, 5- to 7-membered heterocycles optionally containing within the cyclic system a second hetero atom selected from oxygen and nitrogen there may be mentioned, without implying any limitation, pyrrolidinyl, isoxazolidinyl, oxazolidinyl, pyrazolidinyl, imidazolidinyl, piperidyl, oxazinanyl, morpholinyl, hexahydropyridazinyl, hexahydropyrimidinyl, piperazinyl, azepanyl, oxazepanyl and diazepanyl groups.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid, lysine etc.

Among the pharmaceutically acceptable bases there may be mentioned, without implying any limitation, sodium hydroxide, potassium hydroxide, triethylamine, tert-butylamine etc.

As substituents X and Y preference is given, in accordance with the invention, to hydrogen atoms.

As substituents $R_1$, $R_3$ and $R_4$ preference is given, in accordance with the invention, to linear or branched ($C_1$–$C_6$) alkyl groups.

As the substituent $R_2$ preference is given, in accordance with the invention, to the group —$OR_a$ wherein $R_a$ is as defined for formula (I).

As the substituent $R_5$ preference is given, in accordance with the invention, to the group —$OR_c$ wherein $R_c$ is as defined for formula (I) and to the group $W_1$—($W_2$)—U—V wherein $W_1$, $W_2$, U and V are as defined for formula (I).

As the substituent $R_5$ even greater preference is given, in accordance with the invention, to the group —$OR_c$ wherein $R_c$ represents a hydrogen atom and to the group $W_1$—C ($W_2$)—U—V wherein $W_1$ and $W_2$ each represent an oxygen atom, U represents a linear or branched ($C_1$–$C_8$)alkylene chain and V represents a hydrogen atom.

As the substituent Z preference is given, in accordance with the invention, to an oxygen atom.

As the substituent Ar preference is given, in accordance with the invention, to an optionally substituted phenyl group.

In especially advantageous manner, preferred compounds of the invention are:
  (±)-cis-2-cinnamoyloxy-1-hydroxy-6-methoxy-3,3,14-trimethyl-1,2,3,14-tetrahydro-1H-benzo[b]pyrano[3,2-h]acridin-7-one,
  (±)-cis-1-acetoxy-2-cinnamoyloxy-6-methoxy-3,3,14-trimethyl-1,2,3,14-tetrahydro-1H-benzo[b]pyrano[3,2-h]acridin-7-one,
  (±)-cis-2-(4-chlorocinnamoyloxy)-1-hydroxy-6-methoxy-3,3,14-trimethyl-1,2,3,14-tetrahydro-1H-benzo[b]pyrano[3,2-h]acridin-7-one,
  (±)-cis-1-acetoxy-2-(4-chlorocinnamoyloxy)-6-methoxy-3,3,14-trimethyl-1,2,3,14-tetrahydro-1H-benzo[b]pyrano[3,2-h]acridin-7-one,
  (±)-cis-2-(2-chlorocinnamoyloxy)-1-hydroxy-6-methoxy-3,3,14-trimethyl-1,2,3,14-tetrahydro-1H-benzo[b]pyrano[3,2-h]acridin-7-one,
  (±)-cis-1-acetoxy-2-(2-chlorocinnamoyloxy)-6-methoxy-3,3,14-trimethyl-1,2,3,14-tetrahydro-1H-benzo[b]pyrano[3,2-h]acridin-7-one,
  (±)-cis-2-(3-chlorocinnamoyloxy)-1-hydroxy-6-methoxy-3,3,14-trimethyl-1,2,3,14-tetrahydro-1H-benzo[b]pyrano[3,2-h]acridin-7-one,
  (±)-cis-2-(2,4-dichlorocinnamoyloxy)-1-hydroxy-6-methoxy-3,3,14-trimethyl-1,2,3,14-tetrahydro-1H-benzo[b]pyrano[3,2-h]acridin-7-one,
  (±)-cis-1-acetoxy-2-(2,4-dichlorocinnamoyloxy)-6-methoxy-3,3,14-trimethyl-1,2,3,14-tetrahydro-1H-benzo[b]pyrano[3,2-h]acridin-7-one,
  (±)-cis-2-(3,4-dichlorocinnamoyloxy)-1-hydroxy-6-methoxy-3,3,14-trimethyl-1,2,3,14-tetrahydro-1H-benzo[b]pyrano[3,2-h]acridin-7-one,
  (±)-cis-1-acetoxy-2-(3,4-dichlorocinnamoyloxy)-6-methoxy-3,3,14-trimethyl-1,2,3,14-tetrahydro-1H-benzo[b]pyrano[3,2-h]acridin-7-one,
  (±)-cis-2-(4-bromocinnamoyloxy)-1-hydroxy-6-methoxy-3,3,14-trimethyl-1,2,3,14-tetrahydro-1H-benzo[b]pyrano[3,2-h]acridin-7-one,
  (±)-cis-1-acetoxy-2-(4-bromocinnamoyloxy)-6-methoxy-3,3,14-trimethyl-1,2,3,14-tetrahydro-1H-benzo[b]pyrano[3,2-h]acridin-7-one,
  (±)-cis-1-hydroxy-6-methoxy-2-(4-methoxycinnamoyloxy)-3,3,14-trimethyl-1,2,3,14-tetrahydro-1H-benzo[b]pyrano[3,2-h]acridin-7-one, (±)-cis-1-hydroxy-6-methoxy-2-(4-nitrocinnamoyloxy)-3,3,14-trimethyl-1,2,3,14-tetrahydro-1H-benzo[b]pyrano[3,2-h]acridin-7-one, (±)-cis-1-acetoxy-6-methoxy-2-(4-nitrocinnamoyloxy)-3,3,14-trimethyl-1,2,3,14-tetrahydro-1H-benzo[b]pyrano[3,2-h]acridin-7-one.

The present invention relates also to a process for the preparation of compounds of formula (I), which process is characterised in that there is used as starting material a compound of formula (II):

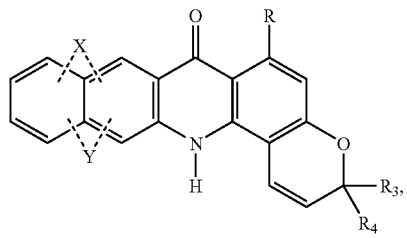

(II)

wherein X, Y, $R_3$ and $R_4$ are as defined hereinbefore and R represents a hydrogen atom, a hydroxy group or a linear or branched ($C_1$–$C_6$)alkyl group, the nitrogen atom of which compound of formula (II) is substituted, or not, by the action of an alkyl halide or of a dialkyl sulphate in the presence of a deprotonating agent, in an aprotic polar solvent or under phase transfer conditions, allowing the compounds of formula (III) to be obtained:

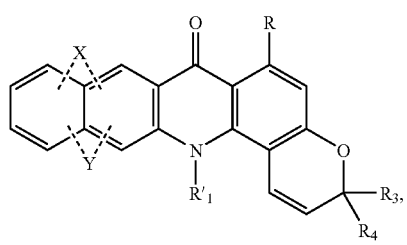

(III)

wherein X, Y, R, $R_3$ and $R_4$ are as defined hereinbefore and $R'_1$ represents a linear or branched ($C_1$–$C_6$)alkyl group, which compounds of formula (III) are subjected to the action of an alkylating agent under customary conditions of organic synthesis to yield the compounds of formula (IV):

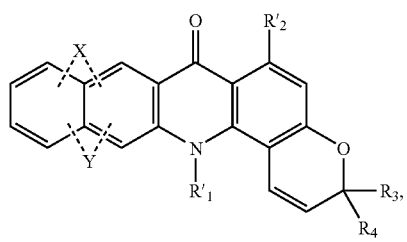

(IV)

wherein X, Y, $R'_1$, $R_3$ and $R_4$ are as defined hereinbefore and $R'_2$ represents a group selected from $OR'_a$ wherein $R'_a$ represents a linear or branched ($C_1$–$C_6$)alkyl group, which compounds of formula (IV), in the case where $R'_2$ represents an alkoxy group, are treated with a compound of formula (V):

$$HNR_aR_b \qquad (V),$$

wherein $R_a$ and $R_b$ are as defined for formula (I), to yield the compounds of formula (VI):

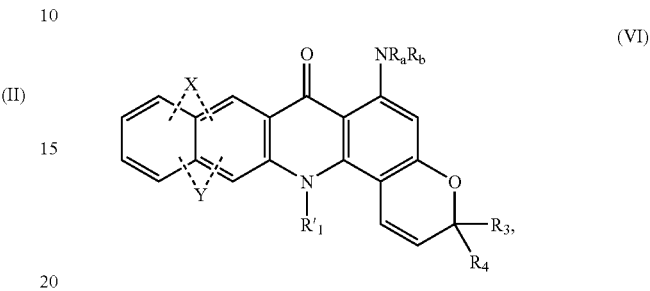

(VI)

wherein X, Y, $R'_1$, $R_3$, $R_4$, $R_a$ and $R_b$ are as defined hereinbefore, the totality of the compounds of formulae (II), (III), (IV) and (VI) forming the compounds of formula (VII):

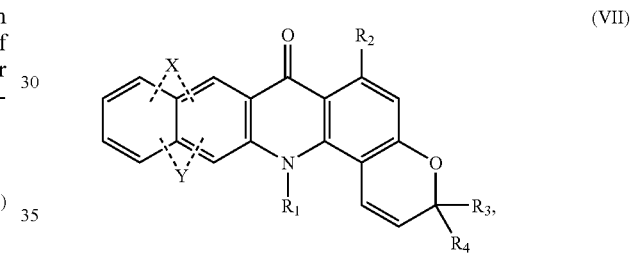

(VII)

wherein X, Y, $R_1$, $R_2$, $R_3$ and $R_4$ are as defined for formula (I), which compounds of formula (VII) are subjected:

a) either to the action of osmium tetroxide in a polar medium and in the presence of 4-methylmorpholine N-oxide to yield the compounds of formula (VIII/a):

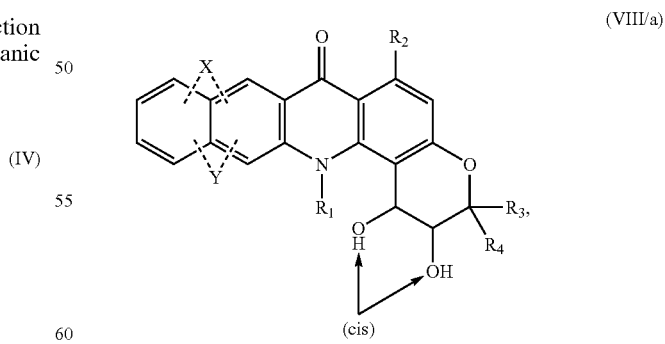

(VIII/a)

(cis)

wherein X, Y, $R_1$, $R_2$, $R_3$ and $R_4$ are as defined hereinbefore, b) or to the action of potassium permanganate in a polar medium and then to reductive conditions in the presence of $NaBH_4$ to yield the compounds of formula (VIII/b):

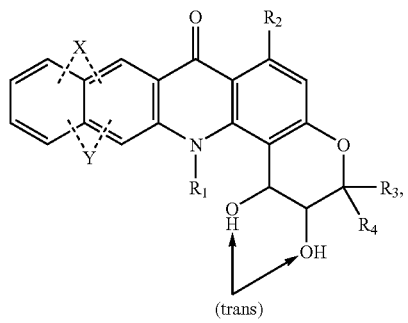

(VIII/b)

(trans)

wherein X, Y, $R_1$, $R_2$, $R_3$ and $R_4$ are as defined hereinbefore, the totality of the compounds of formulae (VIIIa) and (VIII/b) forming the compounds of formula (VIII) wherein the 2 alcohol groups may be of cis or trans configuration with respect to one another:

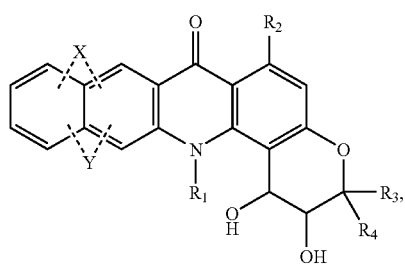

(VIII)

wherein X, Y, $R_1$, $R_2$, $R_3$ and $R_4$ are as defined hereinbefore, which compounds of formula (VIII) are subjected to the action of one or 2 equivalents of an anhydride of formula (IX) or of an acid chloride of formula (X):

 (IX)

 (X), wherein Ar is as defined for formula (I), to yield the compounds of formula (I/a$_1$) or (I/a$_2$), particular cases of the compounds of formula (I):

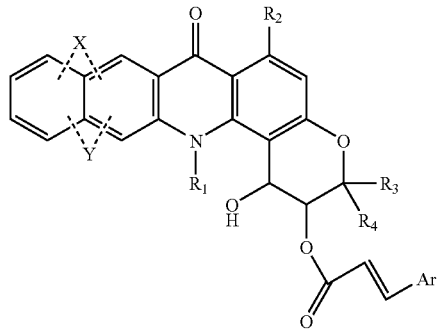

(I/a$_1$)

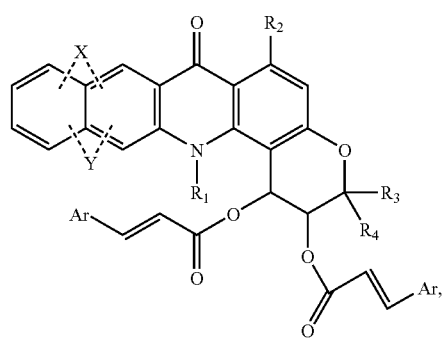

(I/a$_2$)

wherein X, Y, $R_1$, $R_2$, $R_3$, $R_4$ and Ar are as defined hereinbefore, c) or to the action of $NaN_3$, in the presence of hydrogen peroxide, followed by a reduction step to yield the compounds of formula (XI):

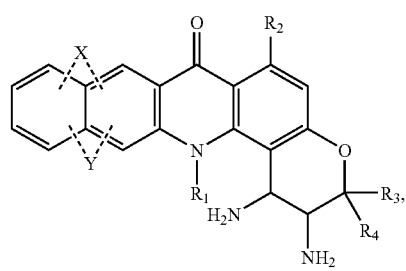

(XI)

wherein X, Y, $R_1$, $R_2$, $R_3$ and $R_4$ are as defined hereinbefore, which compounds of formula (XI) are subjected to the action of compounds of formula (IX) or (X) as defined hereinbefore under the same conditions as for the compounds of formula (VIII) to yield the compounds of formula (I/b$_1$) or (I/b$_2$), particular cases of the compounds of formula (I):

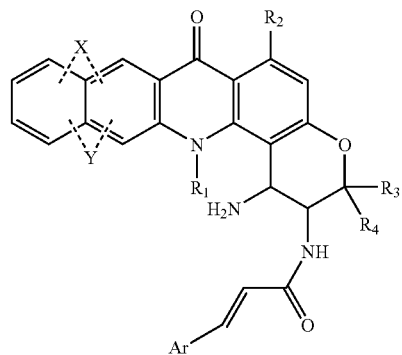

(I/b$_1$)

-continued

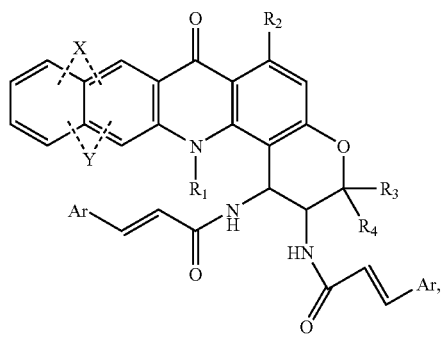
(I/b₂)

wherein X, Y, R₁, R₂, R₃, R₄ and Ar are as defined hereinbefore, which compounds of formula (I/b₁) or (I/b₂) are optionally subjected to the action of a compound of formula (XII):

$$R'_c\text{-Hal} \quad (XII),$$

wherein Hal represents a halogen and R'$_c$ represents a group selected from linear or branched (C₁–C₆)alkyl, an aryl group and aryl-(C₁–C₆)alkyl in which the alkyl moiety is linear or branched, to yield the compounds of formula (I/c₁) or (I/c₂):

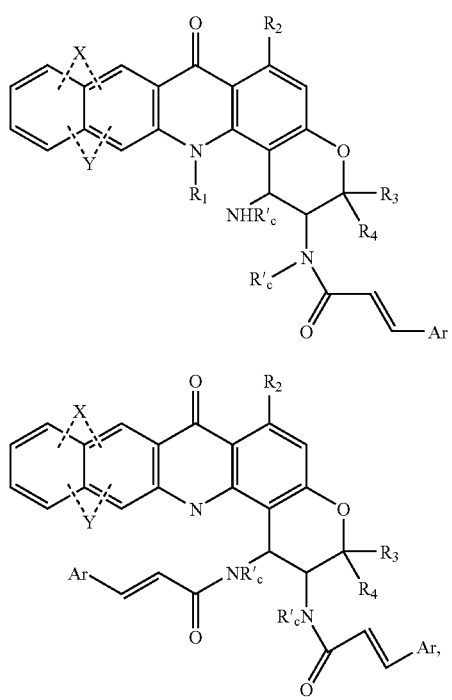
(I/c₁)

(I/c₂)

wherein X, Y, R₁, R₂, R₃, R₄, R'$_c$ and Ar are as defined hereinbefore, the totality of the compounds of formulae (I/a₁), (I/b₁) and (I/c₁), and (I/a₂), (I/b₂) and (I/c₂) forming the compounds of formulae (I/d₁) and (I/d₂), respectively,

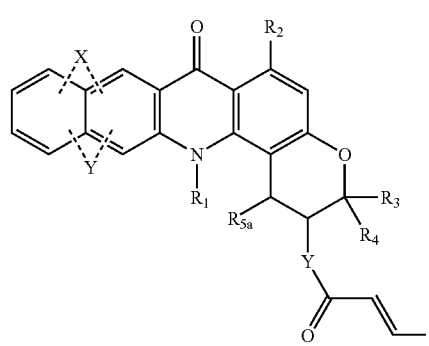
(I/d₁)

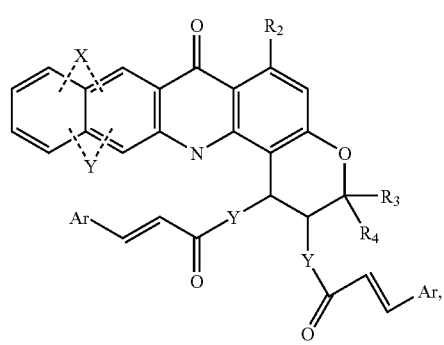
(I/d₂)

wherein X, Y, R₁, R₂, R₃, R₄, Y and Ar are as defined for formula (I) and R$_{5a}$ represents a hydroxy group, NH₂ or NHR'$_c$ wherein R'$_c$ is as defined hereinbefore, which compounds of formula (I/d₁) are optionally subjected:

a) either to the action of an alkylating agent to yield the compounds of formula (I/e), a particular case of the compounds of formula (I)

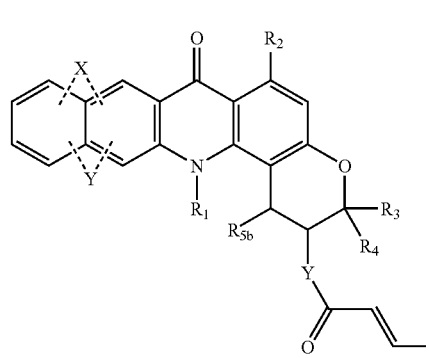
(I/e)

wherein X, Y, R₂, R₂, R₃, R₄, Y and Ar are as defined hereinbefore and R$_{5b}$ represents a group OR$_c$ or NR$_c$R$_d$ wherein R$_c$ and R$_d$ are as defined for formula (I), b) or to the action of an anhydride of formula (XIII) or of an acid chloride of formula (XIV):

$$(R_{10})_2O \quad (XIII)$$

$$R_{10}\text{—Cl} \quad (XIV),$$

wherein R₁₀ represents a group of formula C(W₂)—U—V or C(W₂)—W₃-T₁ wherein W₂, W₃, U, V and T₁ are as defined for formula (I), to yield the compounds of formula (I/f), a particular case of the compounds of formula (I):

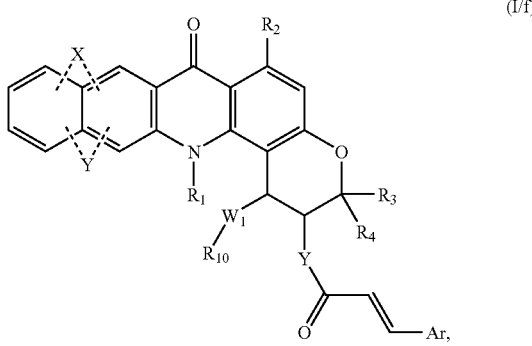

(I/f)

wherein X, Y, R₁, R₂, R₃, R₄, Y, Ar and R₁₀ are as defined hereinbefore and W₁ is as defined for formula (I), the compounds (I/a) to (I/f) constituting the totality of the compounds of the invention, which are purified, if necessary, according to a conventional purification technique, which may be, if desired, separated into their different isomers according to a conventional separation technique and which are converted, if desired, into their addition salts with a pharmaceutically acceptable acid or base.

The compounds of formulae (II), (V), (IX), (X), (XII), (XIII) and (XIV) either are commercially available products or are obtained according to conventional methods of organic synthesis well known to the person skilled in the art.

The compounds of formula (I) have especially valuable anti-tumour properties. They have excellent in vitro cytotoxicity with respect to cell lines originating from murine and human tumours, by virtue of specific blockage of the cell cycle, and are active in vivo, in the mouse, with respect to transplantable murine and human tumours. The characteristic properties of these compounds allow them to be used therapeutically as anti-tumour agents.

The present invention relates also to pharmaceutical compositions comprising, as active ingredient, at least one compound of formula (I), an enantiomer or diastereoisomer thereof, or an addition salt thereof with a pharmaceutically acceptable acid or base, alone or in combination with one or more inert, non-toxic, pharmaceutically acceptable excipients or carriers.

Among the pharmaceutical compositions according to the invention there may be mentioned more especially those that are suitable for oral, parenteral (intravenous, intramuscular or subcutaneous), per- or trans-cutaneous, intravaginal, rectal, nasal, perlingual, buccal, ocular or respiratory administration.

Pharmaceutical compositions according to the invention for parenteral injections especially include aqueous and non-aqueous sterile solutions, dispersions, suspensions or emulsions and also sterile powders for reconstituting injectable solutions or dispersions.

Pharmaceutical compositions according to the invention for solid oral administration especially include tablets or dragees, sublingual tablets, sachets, gelatin capsules and granules, and for liquid oral, nasal, buccal or ocular administration especially include emulsions, solutions, suspensions, drops, syrups and aerosols.

Pharmaceutical compositions for rectal or vaginal administration are preferably suppositories and those for per- or trans-cutaneous administration especially include powders, aerosols, creams, ointments, gels and patches.

The pharmaceutical compositions mentioned hereinbefore illustrate the invention but do not limit it in any way.

Among the inert, non-toxic, pharmaceutically acceptable excipients or carriers there may be mentioned, by way of non-limiting example, diluents, solvents, preservatives, wetting agents, emulsifiers, dispersing agents, binders, swelling agents, disintegrating agents, retardants, lubricants, absorbents, suspending agents, colourants, aromatising agents etc.

The useful dosage varies according to the age and weight of the patient, the administration route, the pharmaceutical composition used, the nature and severity of the disorder and the administration of any associated treatments. The dosage ranges from 0.1 mg to 1000 mg per day in one or more administrations.

The Examples that follow illustrate the invention but do not limit it in any way.

The starting materials used are products that are known or that are prepared according to known operating procedures. The various Preparations yield synthesis intermediates that are useful in preparation of the compounds of the invention.

The structures of the compounds described in the Examples and Preparations were determined according to the usual spectrophotometric techniques (infrared, nuclear magnetic resonance, mass spectrometry, . . . ).

The melting points were determined using either a Kofler hot-plate or a hot-plate under a microscope. When the compound is in the form of a salt, the melting point given refers to that of the salt form of the compound.

PREPARATION 1

4-Chlorocinnamoyl Chloride 7 ml of thionyl chloride are added dropwise to a suspension of 1.75 g of 4-chlorocinnamic acid in 40 ml of anhydrous dichloromethane, with stirring at 43° C. After reacting for 3 hours, the excess acid that has not reacted remains undissolved and is removed by decanting. The filtrate is evaporated to dryness, yielding 4-chlorocinnamic acid chloride.

PREPARATION 2

2-Chlorocinnamoyl Chloride

The product is obtained according to the procedure of Preparation 1, using 2-chlorocinnamic acid instead of 4-chlorocinnamic acid.

PREPARATION 3

3-Chlorocinnamoyl Chloride

The product is obtained according to the procedure of Preparation 1, using 3-chlorocinnamic acid instead of 4-chlorocinnamic acid.

PREPARATION 4

2,4-Dichlorocinnamoyl Chloride

The product is obtained according to the procedure of Preparation 1, using 2,4-dichlorocinnamic acid instead of 4-chlorocinnamic acid.

PREPARATION 5

3,4-Dichlorocinnamoyl Chloride

The product is obtained according to the procedure of Preparation 1, using 3,4-dichlorocinnamic acid instead of 4-chlorocinnamic acid.

PREPARATION 6

4-Bromocinnamoyl Chloride

The product is obtained according to the procedure of Preparation 1, using 4-bromocinnamic acid instead of 4-chlorocinnamic acid.

PREPARATION 7

4-Methoxycinnamoyl Chloride

The product is obtained according to the procedure of Preparation 1, using 4-methoxycinnamic acid instead of 4-chlorocinnamic acid.

PREPARATION 8

4-Nitrocinnamoyl Chloride

The product is obtained according to the procedure of Preparation 1, using 4-nitrocinnamic acid instead of 4-chlorocinnamic acid.

PREPARATION 9

4-Fluorocinnamoyl Chloride

The product is obtained according to the procedure of Preparation 1, using 4-fluorocinnamic acid instead of 4-chlorocinnamic acid.

PREPARATION 10

3,4-Dimethoxycinnamoyl Chloride

The product is obtained according to the procedure of Preparation 1, using 3,4-dimethoxycinnamic acid instead of 4-chlorocinnamic acid.

PREPARATION 11

3-Trifluoromethylcinnamoyl Chloride

The product is obtained according to the procedure of Preparation 1, using 3-trifluoromethylcinnamic acid instead of 4-chlorocinnamic acid.

PREPARATION 12

3-Bromocinnamoyl Chloride

The product is obtained according to the procedure of Preparation 1, using 3-bromocinnamic acid instead of 4-chlorocinnamic acid.

PREPARATION 13

4-Trifluoromethylcinnamoyl Chloride

The product is obtained according to the procedure of Preparation 1, using 4-trifluoromethylcinnamic acid instead of 4-chlorocinnamic acid.

PREPARATION 14

3-(1-Naphthyl)acryloyl Chloride

The product is obtained according to the procedure of Preparation 1, using 3-(1-naphthyl)acrylic acid instead of 4-chlorocinnamic acid.

PREPARATION 15

3-(2-Naphthyl)acryloyl Chloride

The product is obtained according to the procedure of Preparation 1, using 3-(2-naphthyl)acrylic acid instead of 4-chlorocinnamic acid.

EXAMPLE 1

(±)-cis-2-Cinnamoyloxy-1-hydroxy-6-methoxy-3,3,14-trimethyl-1,2,3,14-tetrahydro-1H-benzo[b]pyrano[3,2-h]acridin-7-one 619 mg of cinnamoyl chloride are added to a solution of 520 mg of (±)cis-1,2-dihydroxy-6-methoxy-3,3,14-trimethyl-2,3,7,14-tetrahydro-1H-benzo[b]pyrano[3,2-h]acridin-6-one (EP 1 042 326) in 15 ml of anhydrous pyridine. After stirring for 48 hours at 20° C., the solvent is evaporated off to dryness under reduced pressure at a temperature not exceeding 20° C. Chromatography over silica gel (dichloromethane and then a methanol gradient from 0.2 to 1%) followed by precipitation from ethanol allows 233 mg of the expected product to be isolated.

Mass spectrometry (DIC/NH$_3$): m/z=536 [MH]$^+$

EXAMPLE 2

(±)-cis-1-Acetoxy-2-cinnamoyloxy-6-methoxy-3,3,14-trimethyl-1,2,3,14-tetrahydro-1H-benzo[b]pyrano[3,2-h]acridin-7-one 3 ml of acetic anhydride and 7 mg of 4-dimethylaminopyridine are added to a solution of 170 mg of the compound of Example 1 in 5 ml of anhydrous pyridine. The reaction mixture is stirred at ambient temperature for 5 hours and is then poured into 20 ml of ice-cold water. The precipitate obtained is filtered off, washed with water and dried under vacuum over phosphorus pentoxide, allowing 130 mg of the expected product to be isolated.

Mass spectrometry (ES$^+$): m/z=578 [MH]$^+$

EXAMPLE 3

(±)-cis-2-(4-Chlorocinnamoyloxy)-1-hydroxy-6-methoxy-3,3,14-trimethyl-1,2,3,14-tetrahydro-1H-benzo[b]pyrano[3,2-h]acridin-7-one The product is obtained according to the procedure of Example 1, using the compound of Preparation 1 instead of cinnamoyl chloride.

Mass spectrometry (ES$^+$): m/z=569 and 571 [MH]$^+$

EXAMPLE 4

(±)-cis-1-Acetoxy-2-(4-chlorocinnamoyloxy)-6-methoxy-3,3,14-trimethyl-1,2,3,14-tetrahydro-1H-benzo[b]pyrano[3,2-h]acridin-7-one The product is obtained according to the procedure of Example 2, using the compound of Example 3.

Mass spectrometry (ES$^+$): m/z=612 and 614 [MH]$^+$

EXAMPLE 5

(±)-cis-2-(2-Chlorocinnamoyloxy)-1-hydroxy-6-methoxy-3,3,14-trimethyl-1,2,3,14-tetrahydro-1H-benzo[b]pyrano[3,2-h]acridin-7-one The product is obtained according to the procedure of Example 1, using the compound of Preparation 2 instead of cinnamoyl chloride.

Mass spectrometry (ES$^+$): m/z=570 and 572 [MH]$^+$

EXAMPLE 6

(±)-cis-1-Acetoxy-2-(2-chlorocinnamoyloxy)-6-methoxy-3,3,14-trimethyl-1,2,3,14-tetrahydro-1H-benzo[b]pyrano[3,2-h]acridin-7-one The product is obtained according to the procedure of Example 2, using the compound of Example 5.

Mass spectrometry (ES$^+$): m/z=612 and 614 [MH]$^+$

EXAMPLE 7

(±)-cis-2-(3-Chlorocinnamoyloxy)-1-hydroxy-6-methoxy-3,3,14-trimethyl-1,2,3,14-tetrahydro-1H-benzo[b]pyrano[3,2-h]acridin-7-one The product is obtained according to the procedure of Example 1, using the compound of Preparation 3 instead of cinnamoyl chloride.

Mass spectrometry (ES$^+$): m/z=570 and 572 [MH]$^+$

EXAMPLE 8

(±)-cis-1-Acetoxy-2-(3-chlorocinnamoyloxy)-6methoxy-3,3,14-trimethyl-1,2,3,14-tetrahydro-1H-benzo[b]pyrano[3,2-h]acridin-7-one The product is obtained according to the procedure of Example 2, using the compound of Example 7.

Mass spectrometry (ES$^+$): m/z=612 and 614 [MH]$^+$

EXAMPLE 9

(±)-cis-2-(2,4-Dichlorocinnamoyloxy)-1-hydroxy-6-methoxy-3,3,14-trimethyl-1,2,3,14-tetrahydro-1H-benzo[b]pyrano[3,2-h]acridin-7-one The product is obtained according to the procedure of Example 1, using the compound of Preparation 4 instead of cinnamoyl chloride.

Mass spectrometry (ES$^+$): m/z=604, 606 and 608 [MH]$^+$

EXAMPLE 10

(±)-cis-1-Acetoxy-2-(2,4-dichlorocinnamoyloxy)-6-methoxy-3,3,14-trimethyl-1,2,3,14-tetrahydro-1H-benzo[b]pyrano[3,2-h]acridin-7-one The product is obtained according to the procedure of Example 2, using the compound of Example 9.

Mass spectrometry (ES$^+$): m/z=646, 648 and 650 [MH]$^+$

EXAMPLE 11

(±)-cis-2-(3,4-Dichlorocinnamoyloxy)-1-hydroxy-6-methoxy-3,3,14-trimethyl-1,2,3,14-tetrahydro-1H-benzo[b]pyrano[3,2-h]acridin-7-one The product is obtained according to the procedure of Example 1, using the compound of Preparation 5 instead of cinnamoyl chloride.

Mass spectrometry (ES$^+$): m/z=604, 606 and 608 [MH]$^+$

EXAMPLE 12

(±)cis-1-Acetoxy-2-(3,4-dichlorocinnamoyloxy)-6methoxy-3,3,14-trimethyl-1,2,3,14-tetrahydro-1H-benzo[b]pyrano[3,2-h]acridin-7-one The product is obtained according to the procedure of Example 2, using the compound of Example 11.

Mass spectrometry (ES$^+$): m/z=646, 648 and 650 [MH]$^+$

EXAMPLE 13

(±)-cis-2-(4-Bromocinnamoyloxy)-1-hydroxy-6-methoxy-3,3,14-trimethyl-1,2,3,14-tetrahydro-1H-benzo[b]pyrano[3,2-h]acridin-7-one The product is obtained according to the procedure of Example 1, using the compound of Preparation 6 instead of cinnamoyl chloride.

Mass spectrometry (ES$^+$): m/z=614 and 616 [MH]$^+$

EXAMPLE 14

(±)-cis-1-Acetoxy-2-(4-bromocinnamoyloxy)-6-methoxy-3,3,14-trimethyl-1,2,3,14-tetrahydro-1H-benzo[b]pyrano[3,2-h]acridin-7-one The product is obtained according to the procedure of Example 2, using the compound of Example 13.

Mass spectrometry (ES$^+$): m/z=656 and 658 [MH]$^+$

EXAMPLE 15

(±)-cis-1-Hydroxy-6-methoxy-2-(4-methoxycinnamoyloxy)-3,3,14-trimethyl-1,2,3,14-tetrahydro-1H-benzo[b]pyrano[3,2-h]acridin-7-one The product is obtained according to the procedure of Example 1, using the compound of Preparation 7 instead of cinnamoyl chloride.
Mass spectrometry (ES$^+$): m/z=566 [MH]$^+$

EXAMPLE 16

(±)-cis-1-Acetoxy-6-methoxy-2-(4-methoxycinnamoyloxy)-3,3,14-trimethyl-1,2,3,14-tetrahydro-1H-benzo[b]pyrano[3,2-h]acridin-7-one The product is obtained according to the procedure of Example 2, using the compound of Example 15.
Mass spectrometry (ES$^+$): m/z=608 [MH]$^+$

EXAMPLE 17

(±)cis-6Methoxy-1,2-di-(4-methoxycinnamoyloxy)-3,3,14-trimethyl-1,2,3,14-tetrahydro-1H-benzo[b]pyrano[3,2-h]acridin-7-one The product is obtained in the course of the procedure described in Example 15.
Mass spectrometry (ES$^+$): m/z=726 [MH]$^+$

EXAMPLE 18

(±)-cis-1-Hydroxy-6-methoxy-2-(4-nitrocinnamoyloxy)-3,3,14-trimethyl-1,2,3,14-tetrahydro-1H-benzo[b]pyrano[3,2-h]acridin-7-one The product is obtained according to the procedure of Example 1, using the compound of Preparation 8 instead of cinnamoyl chloride.
Mass spectrometry (ES$^+$): m/z=581 [MH]$^+$

EXAMPLE 19

(±)-cis-1-Acetoxy-6-methoxy-2-(4-nitrocinnamoyloxy)-3,3,14-trimethyl-1,2,3,14-tetrahydro-1H-benzo[b]pyrano[3,2-h]acridin-7-one The product is obtained according to the procedure of Example 2, using the compound of Example 18.
Mass spectrometry (ES$^+$): m/z=623 [MH]$^+$

EXAMPLE 20

(±)cis-1,2-Di-(4-fluorocinnamoyloxy)-6-methoxy-3,3,14-trimethyl-1,2,3,14-tetrahydro-1H-benzo[b]pyrano[3,2-h]acridin-7-one The product is obtained according to the procedure of Example 1, using the compound of Preparation 9 instead of cinnamoyl chloride.
Mass spectrometry (ES$^+$): m/z=703 [MH]$^+$

EXAMPLE 21

(±)-cis-2-(3,4-Dimethoxycinnamoyloxy)-1-hydroxy-6-methoxy-3,3,14-trimethyl-1,2,3,14-tetrahydro-7H-benzo[b]pyrano[3,2-h]acridin-7-one The product is obtained according to the procedure of Example 1, using the compound of Preparation 10 instead of cinnamoyl chloride.
Mass spectrometry (ES$^+$): m/z=596 [MH]$^+$

EXAMPLE 22

(±)-cis-1-Acetoxy-2-(3,4-dimethoxycinnamoyloxy)-6-methoxy-3,3,14-trimethyl-1,2,3,14-tetrahydro-7H-benzo[b]pyrano[3,2-h]acridin-7-one The product is obtained according to the procedure of Example 2, using the compound of Example 21.
Mass spectrometry (ES$^+$): m/z=638 [MH]$^+$

EXAMPLE 23

(±)-cis-1-Hydroxy-6-methoxy-2-(3-trifluoromethylcinnamoyloxy)-3,3,14-trimethyl-1,2,3,14-tetrahydro-7H-benzo[b]pyrano[3,2-h]-acridin-7-one The product is obtained according to the procedure of Example 1, using the compound of Preparation 11 instead of cinnamoyl chloride.
Mass spectrometry (ES$^+$): m/z=604, 605 [MH]$^+$

EXAMPLE 24

(±)-cis-1-Acetoxy-6-methoxy-2-(3-trifluoromethylcinnamoyloxy)-3,3,14-trimethyl-1,2,3,14-tetrahydro-7H-benzo[b]pyrano[3,2-h]-acridin-7-one The product is obtained according to the procedure of Example 2, using the compound of Example 23.
Mass spectrometry (ES$^+$): m/z=646, 647 [MH]$^+$

EXAMPLE 25

(±)-cis-2-(3-Bromocinnamoyloxy)-1-hydroxy-6-methoxy-3,3,14-trimethyl-1,2,3,14-tetrahydro-7H-benzo[b]pyrano[3,2-h]acridin-7-one The product is obtained according to the procedure of Example 1, using the compound of Preparation 12 instead of cinnamoyl chloride.
Mass spectrometry (ES$^+$): m/z=614, 616 [MH]$^+$; 636, 638 [MNa]$^+$

EXAMPLE 26

(±)-cis-1-Acetoxy-2-(3-bromocinnamoyloxy)-6-methoxy-3,3,14-trimethyl-1,2,3,14-tetrahydro-7H-benzo[b]pyrano[3,2-h]acridin-7-one The product is obtained according to the procedure of Example 2, using the compound of Example 25.
Mass spectrometry (ES$^+$): m/z=656, 658 [MH]$^+$

EXAMPLE 27

(±)-cis-1-Hydroxy-6-methoxy-2-(4-trifluoromethyl-cinnamoyloxy)-3,3,14-trimethyl-1,2,3,14-tetrahydro-7H-benzo[b]pyrano[3,2-h]-acridin-7-one The product is obtained according to the procedure of Example 1, using the compound of Preparation 13 instead of cinnamoyl chloride.

Mass spectrometry (ES$^+$): m/z=604, 605 [MH]$^+$

EXAMPLE 28

(±)-cis-1-Acetoxy-6-methoxy-2-(4-trifluoromethyl-cinnamoyloxy)-3,3,14-trimethyl-1,2,3,14-tetrahydro-7H-benzo[b]pyrano[3,2-h]-acridin-7-one The product is obtained according to the procedure of Example 2, using the compound of Example 27.

Mass spectrometry (ES$^+$): m/z=646, 647 [MH]$^+$

EXAMPLE 29

(±)-cis-1-Hydroxy-6-methoxy-2-(3-(1-naphthyl)-acryloyloxy)-3,3,14-trimethyl-1,2,3,14-tetrahydro-7H-benzo[b]pyrano[3,2-h]-acridin-7-one The product is obtained according to the procedure of Example 1, using the compound of Preparation 14 instead of cinnamoyl chloride.

Mass spectrometry (ES$^+$): m/z=586 [MH]$^+$

EXAMPLE 30

(±)-cis-1-Acetoxy-6-methoxy-2-(3-1-naphthylacryloyloxy)-3,3,14-trimethyl-1,2,3,14-tetrahydro-7H-benzo[b]pyrano[3,2-h]-acridin-7-one The product is obtained according to the procedure of Example 2, using the compound of Example 29.

Mass spectrometry (ES$^+$): m/z=628 [MH]$^+$

EXAMPLE 31

(±)-cis-1-Hydroxy-6-methoxy-2-(3-(2-naphthyl)acryloyolxy)-3,3,14-trimethyl-1,2,3,14-tetrahydro-7H-benzo[b]pyrano[3,2-h]-acridin-7-one The product is obtained according to the procedure of Example 1, using the compound of Preparation 15 instead of cinnamoyl chloride.

Mass spectrometry (ES$^+$): m/z=586 [MH]$^+$

EXAMPLE 32

(±)-cis-1-Acetoxy-2-(3,4-dichlorocinnamoyloxy)-6-methoxy-3,3,14-trimethyl-1,2,3,14-tetrahydro-1H-benzo[b]pyrano[3,2-h]acridin-7-one (Enantiomer α)

The α enantiomer of compound of example 12 is obtained by chiral column chiralcel oc separation.

EXAMPLE 33

(±)-cis-1-Acetoxy-2-(3,4-dichlorocinnamoyloxy)-6-methoxy-3,3,14-trimethyl-1,2,3,14-tetrahydro-1H-benzo[b]pyrano[3,2-h]acridin-7-one (Enantiomer β)

The β enantiomer of compound of example 12 is obtained by chiral column chiralcel oc separation.

PHARMACOLOGICAL STUDY OF COMPOUNDS OF THE INVENTION

EXAMPLE A

In vitro Cytotoxicity

Two cell lines were used
1 murine leukaemia: L1210,
1 human epidermoid carcinoma: KB-3-1

The cells are cultured in RPMI 1640 complete culture medium containing 10% foetal calf serum, 2 mM glutamine, 50 units/ml of penicillin, 50 μg/ml of streptomycin and 10 mM Hepes, pH=7.4. The cells are distributed on microplates and are exposed to the cytotoxic compounds. The cells are then incubated for 2 days (L1210) or 4 days (KB-3-1). The number of viable cells is then quantified by a colorimetric assay, the Microculture Tetrazolium Assay (Cancer Res. 1987, 47, 939–942).

The results are expressed in terms of the $IC_{50}$ (the concentration of cytotoxic agent which inhibits proliferation of the treated cells by 50%). By way of example, the compound of Example 2 has an $IC_{50}$ of 0.59 μM with respect to L1210 and of 0.151 μM with respect to KB-3-1.

EXAMPLE B

In vivo Activity

Anti-tumour Activity with Respect to C38 Adenocarcinoma of the Colon

Tumour fragments of C38 adenocarcinoma of the colon weighing approximately 30 mg were implanted under the skin of B6D2F1 mice (Iffa Credo, France) on day 0.

After growth of the tumour, the mice were divided into control (18 animals) and treated (6 or 7 animals) groups, which were homogeneous with respect to tumour size. The products were administered by the i.v. route once per week for 3 weeks (on days 10, 17 and 24), at their Maximum Tolerated Dose (MTD), MTD/2 and MTD/4.

The tumours were measured twice a week and the tumour volumes were calculated according to the following formula: volume (mm$^3$)=length (mm)×breadth (mm$^2$)/2. The anti-tumour activity is expressed as % T/C:

$$\% \ T/C = \frac{\text{median } Vt/V0 \text{ of the treated animals}}{\text{median } Vt/V0 \text{ of the control animals}} \times 100$$

V0 and Vt being the initial volume of the tumour and its volume at measurement time t, respectively.

The optimum dose is the dose giving the lowest T/C value without toxicity (early death or weight loss greater than 20%).

By way of example, the compounds of Example 33 exhibit an anti-tumour activity of 50% for an optimum dose of 4 mg/kg, whereas acronycine exhibits an anti-tumour activity of 27% for an optimum dose of 100 mg/kg, thereby demonstrating their strong therapeutic potential.

EXAMPLE C

Pharmaceutical Composition

Formula for the preparation of 1000 tablets each comprising 10 mg of active ingredient

| | |
|---|---|
| Compound of Example 2 | 10 g |
| Hydroxypropylcellulose | 2 g |
| Wheat starch | 10 g |
| Lactose | 100 g |
| Magnesium stearate | 3 g |
| Talc | 3 g |

The invention claimed is:
1. A compound selected from those of formula (I):

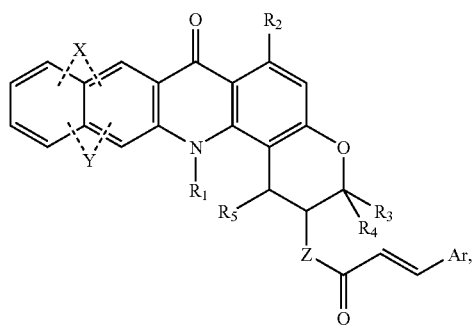

wherein:
X and Y, which may be the same or different, each independently represents a group selected from:
hydrogen, halogen, hydroxy, linear or branched ($C_1$–$C_6$)alkoxy, nitro, cyano, linear or branched ($C_1$–$C_6$)alkyl (optionally substituted by one or more groups selected from hydroxy and halogen), linear or branched ($C_2$–$C_6$)alkenyl, and —$NR_aR_b$ wherein:
$R_a$ and $R_b$, which may be the same or different, each independently represents a group selected from hydrogen and linear or branched ($C_1$–$C_6$)alkyl group, or
$R_a$ and $R_b$, together with the nitrogen atom carrying them, form a monocyclic, 5- to 7-membered heterocycle optionally having in the cyclic system a second heteroatom selected from oxygen and nitrogen,
it being understood that the substituents X and Y may be present, independently of one another, on either of the two adjacent benzene rings,
Z represents oxygen or $NR_c$ wherein $R_c$ represents a group selected from hydrogen, linear or branched ($C_1$–$C_6$) alkyl, aryl and aryl-($C_1$–$C_6$)alkyl group in which the alkyl moiety may be linear or branched,
Ar represents aryl or heteroaryl,
$R_1$ represents hydrogen or linear or branched ($C_1$–$C_6$) alkyl,
$R_2$ represents a group selected from hydrogen, linear or branched ($C_1$–$C_6$)alkyl, —$OR_a$, and —$NR_aR_b$, $R_3$ and $R_4$, which may be the same or different, each independently represents hydrogen or linear or branched ($C_1$–$C_6$)alkyl,
$R_5$ represents a group selected from
hydrogen,
$OR_c$ and $NR_cR_d$ wherein:
$R_d$ is as defined for $R_c$,
$W_1$—$C(W_2)$—U—V wherein:
W represents oxygen or $NR_c$,
$W_2$ represents oxygen,
U represents single bond or linear or branched ($C_1$–$C_8$)alkylene or linear or branched ($C_2$–$C_8$) alkenylene,
V represents a group selected from:
hydrogen,
aryl or heteroaryl,
$OR_c$, $CO_2R_c$, $COR_c$, $CONR'_aR'_b$, $NR'_aR'_b$, $N(R_c)$—$CO_2R'_c$, $N(R_c)$—$COR'_c$ wherein $R'_c$ is as defined for $R_c$, and $R'_a$ and $R'_b$, which may be the same or different, each independently represents a group selected from hydrogen, linear or branched ($C_1$–$C_6$)alkyl, aryl and aryl-($C_1$–$C_6$)alkyl in which the alkyl moiety may be linear or branched or
$R'_a$ and $R'_b$, together with the nitrogen atom carrying them, form a monocyclic, 5- to 7-membered heterocycle optionally having in the cyclic system a second heteroatom selected from oxygen and nitrogen,
$W_1$—$C(W_2)$—$W_3$—$T_1$ wherein:
$W_3$ represents oxygen or $NR_c$,
$T_1$ represents a group selected from:
hydrogen,
linear or branched ($C_1$–$C_6$)alkyl,
linear or branched ($C_2$–$C_6$)alkenyl,
aryl,
aryl-($C_1$–$C_6$)alkyl in which the alkyl moiety may be linear or branched, and
linear or branched ($C_1$–$C_6$)alkylene or linear or branched ($C_2$–$C_6$)alkenylene,
each of which being substituted by a group selected from $OR_c$ and $NR'_aR'_b$, -Z-CO—CH=CHAr,
its enantiomers and diastereoisomers, and addition salts thereof with a pharmaceutically acceptable acid or base,
it being understood that:
"aryl" represents "phenyl" or "naphthyl" each of those groups being optionally substituted by one or more, identical or different, substituents selected from linear or branched ($C_1$–$C_6$)alkyl (optionally substituted by one or more hydroxy or halogen groups), hydroxy, halogen, carboxy, nitro, amino, linear or branched mono($C_1$–$C_6$)alkylamino, di($C_1$–$C_6$)alkylamino wherein each alkyl moiety may be linear or branched, linear or branched ($C_1$–$C_6$)alkoxy, linear or branched ($C_1$–$C_6$)acyl and linear or branched ($C_1$–$C_6$)alkylcarbonyloxy,
"heteroaryl" represents a 5- to 12-membered group which either is monocyclic and aromatic or is bicyclic with at least one of the rings being of aromatic character, and which has one, two or three heteroatoms selected from oxygen, nitrogen and sulphur, it being understood that the heteroaryl group may be optionally substituted by one or more, identical or different, groups selected from halogen, linear or branched ($C_1$–$C_6$)alkyl optionally substituted by one or more hydroxyl groups or halogen atoms, hydroxy, linear or branched $(C_1-C_6)$alkoxy, and amino optionally substituted by one or two linear or branched $(C_1-C_6)$alkyl groups.

2. A compound of claim 1, wherein X and Y each represents hydrogen.

3. A compound of claim 1, wherein $R_1$, $R_3$ and $R_4$ represent linear or branched $(C_1-C_6)$alkyl.

4. A compound of claim 1, wherein $R_2$ represents —$OR_a$.

5. A compound of claim 1, wherein $R_5$ represents —$OR_c$ or $W_1$—$C(W_2)$—U—V.

6. A compound of claim 1, wherein $R_5$ represents —$OR_c$ wherein $R_c$ represents hydrogen or $R_5$ represents $W_1$—C$(W_2)$—U—V wherein $W_1$ and $W_2$ each represent oxygen, U represents linear or branched $(C_1-C_8)$alkylene and V represents hydrogen.

7. A compound of claim 1, wherein Z represents oxygen.

8. A compound of claim 1, wherein Ar represents optionally substituted phenyl.

9. A compound of claim 1, which is selected from:
- (±)-cis-2-cinnamoyloxy-1-hydroxy-6-methoxy-3,3,14-trimethyl-1,2,3,14-tetrahydro-1H-benzo[b]pyrano[3,2-h]acridin-7-one,
- (±)-cis-1-acetoxy-2-cinnamoyloxy-6-methoxy-3,3,14-trimethyl-1,2,3,14-tetrahydro-1H-benzo[b]pyrano[3,2-h]acridin-7-one,
- (±)-cis-2-(4-chlorocinnamoyloxy)-1-hydroxy-6-methoxy-3,3,14-trimethyl-1,2,3,14-tetrahydro-1H-benzo[b]pyrano[3,2-h]acridin-7-one,
- (±)-cis-1-acetoxy-2-(4-chlorocinnamoyloxy)-6-methoxy-3,3,14-trimethyl-1,2,3,14-tetrahydro-1H-benzo[b]pyrano[3,2-h]acridin-7-one,
- (±)-cis-2-(2-chlorocinnamoyloxy)-1-hydroxy-6-methoxy-3,3,14-trimethyl-1,2,3,14-tetrahydro-1H-benzo[b]pyrano[3,2-h]acridin-7-one,
- (±)-cis-1-acetoxy-2-(2-chlorocinnamoyloxy)-6-methoxy-3,3,14-trimethyl-1,2,3,14-tetrahydro-1H-benzo[b]pyrano[3,2-h]acridin-7-one,
- (±)-cis-2-(3-chlorocinnamoyloxy)-1-hydroxy-6-methoxy-3,3,14-trimethyl-1,2,3,14-tetrahydro-1H-benzo[b]pyrano[3,2-h]acridin-7-one,
- (±)-cis-2-(2,4-dichlorocinnamoyloxy)-1-hydroxy-6-methoxy-3,3,14-trimethyl-1,2,3,14-tetrahydro-1H-benzo[b]pyrano[3,2-h]acridin-7-one,
- (±)-cis-1-acetoxy-2-(2,4-dichlorocinnamoyloxy)-6-methoxy-3,3,14-trimethyl-1,2,3,14-tetrahydro-1H-benzo[b]pyrano[3,2-h]acridin-7-one,
- (±)-cis-2-(3,4-dichlorocinnamoyloxy)-1-hydroxy-6-methoxy-3,3,14-trimethyl-1,2,3,14-tetrahydro-1H-benzo[b]pyrano[3,2-h]acridin-7-one,
- (±)-cis-1-acetoxy-2-(3,4-dichlorocinnamoyloxy)-6-methoxy-3,3,14-trimethyl-1,2,3,14-tetrahydro-1H-benzo[b]pyrano[3,2-h]acridin-7-one,
- (±)-cis-2-(4-bromocinnamoyloxy)-1-hydroxy-6-methoxy-3,3,14-trimethyl-1,2,3,14-tetrahydro-1H-benzo[b]pyrano[3,2-h]acridin-7-one,
- (±)-cis-1-acetoxy-2-(4-bromocinnamoyloxy)-6-methoxy-3,3,14-trimethyl-1,2,3,14-tetrahydro-1H-benzo[b]pyrano[3,2-h]acridin-7-one,
- (±)-cis-1-hydroxy-6-methoxy-2-(4-methoxycinnamoyloxy)-3,3,14-trimethyl-1,2,3,14-tetrahydro-1H-benzo[b]pyrano[3,2-h]acridin-7-one,
- (±)-cis-1-hydroxy-6-methoxy-2-(4-nitrocinnamoyloxy)-3,3,14-trimethyl-1,2,3,14-tetrahydro-1H-benzo[b]pyrano[3,2-h]acridin-7-one, and
- (±)-cis-1-acetoxy-6-methoxy-2-(4-nitrocinnamoyloxy)-3,3,14-trimethyl-1,2,3,14-tetrahydro-1H-benzo[b]pyrano[3,2-h]acridin-7-one.

10. A method for treating a living animal body, afflicted with a condition selected from leukemia, epidermoid carcinoma, and adenocarcinoma of the colon, comprising the step of administering to the living animal body an amount of a compound of claim 1, which is effective for treatment of the condition.

11. A pharmaceutical composition comprising as active principle an effective amount of a compound of claim 1, together with one or more pharmaceutically acceptable excipients or vehicles.

12. The method of claim 10, wherein the living animal body is a human.

* * * * *